US008038709B2

(12) United States Patent
Palasis et al.

(10) Patent No.: US 8,038,709 B2
(45) Date of Patent: Oct. 18, 2011

(54) LOCAL DELIVERY OF THERAPEUTIC AGENT TO HEART VALVES

(75) Inventors: Maria Palasis, Wellesley, MA (US); Timothy J. Mickley, Elk River, MN (US); Toby Freyman, Waltham, MA (US); Wendy Naimark, Boston, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 323 days.

(21) Appl. No.: 12/022,413

(22) Filed: Jan. 30, 2008

(65) Prior Publication Data
US 2008/0183143 A1    Jul. 31, 2008

Related U.S. Application Data

(60) Provisional application No. 60/898,099, filed on Jan. 30, 2007.

(51) Int. Cl.
*A61F 2/06* (2006.01)
*A61M 31/00* (2006.01)
(52) U.S. Cl. .................. 623/1.42; 623/1.26; 604/500
(58) Field of Classification Search .......... 604/200, 604/265, 507; 623/1.1, 1.13, 1.15, 1.24, 623/1.38, 1.42, 2.1, 2.11, 2.12, 2.14, 2.18, 623/2.36
See application file for complete search history.

(56) References Cited

U.S. PATENT DOCUMENTS

| 5,091,205 | A | | 2/1992 | Fan |
| 5,554,185 | A | * | 9/1996 | Block et al. ............. 623/2.12 |
| 5,667,523 | A | * | 9/1997 | Bynon et al. ............ 623/1.13 |
| 6,254,632 | B1 | | 7/2001 | Wu |
| 6,425,916 | B1 | * | 7/2002 | Garrison et al. ......... 623/2.11 |
| 6,626,899 | B2 | | 9/2003 | Houser et al. |
| 6,676,698 | B2 | * | 1/2004 | McGuckin et al. ...... 623/1.24 |
| 7,186,262 | B2 | | 3/2007 | Saadat |
| 7,217,284 | B2 | | 5/2007 | Houser et al. |
| 7,419,696 | B2 | * | 9/2008 | Berg et al. ............... 427/2.24 |
| 7,534,259 | B2 | * | 5/2009 | Lashinski et al. ........ 623/2.1 |
| 7,562,660 | B2 | | 7/2009 | Saadat |
| 7,658,727 | B1 | | 2/2010 | Fernandes et al. |

(Continued)

FOREIGN PATENT DOCUMENTS

EP    2 121 106    11/2009

(Continued)

OTHER PUBLICATIONS

International Search Report and Written Opinion (PCT/US2008/001160), dated Oct. 22, 2008.

(Continued)

*Primary Examiner* — Theodore Stigell
*Assistant Examiner* — William Carpenter
(74) *Attorney, Agent, or Firm* — Fish & Richardson P.C.

(57) ABSTRACT

The present invention relates to implantable medical devices and methods that employ these medical devices to treat heart valves. In one embodiment, a medical device is provided comprising a body. The body may have a portion thereof including therapeutic agent and can be configured to support the device proximate a heart valve. Methods in accordance with embodiments of the present invention may also include providing a medical device having a body with at least a portion thereof including a therapeutic agent. These methods may also include positioning the medical device in a location proximate to a downstream surface of the heart valve and securing the device. The therapeutic agent released may then be delivered to the heart valve.

19 Claims, 14 Drawing Sheets

U.S. PATENT DOCUMENTS

| | | |
|---|---|---|
| 7,753,922 B2 | 7/2010 | Starksen |
| 2003/0028243 A1 | 2/2003 | Bates et al. |
| 2004/0106987 A1 | 6/2004 | Palasis et al. |
| 2005/0055087 A1 | 3/2005 | Starksen |
| 2005/0084515 A1* | 4/2005 | Udipi et al. .................... 424/426 |
| 2005/0222661 A1* | 10/2005 | Case et al. ..................... 623/1.1 |
| 2005/0267556 A1* | 12/2005 | Shuros et al. ................. 607/120 |
| 2006/0286139 A1* | 12/2006 | Ai-Lamee et al. ............. 424/423 |
| 2007/0027460 A1* | 2/2007 | Case et al. ..................... 606/151 |
| 2007/0112422 A1* | 5/2007 | Dehdashtian ................ 623/2.11 |
| 2008/0183413 A1* | 7/2008 | Deshpande et al. ............ 702/99 |

FOREIGN PATENT DOCUMENTS

| | | |
|---|---|---|
| JP | 2010-516426 | 5/2010 |
| WO | 2007/016122 A2 | 2/2007 |
| WO | 2008/094548 | 8/2008 |

OTHER PUBLICATIONS

International Preliminary Report on Patentability issued on Aug. 13, 2009, in the related PCT application PCT/US2008/001160, filed on Jan. 30, 2008.

* cited by examiner

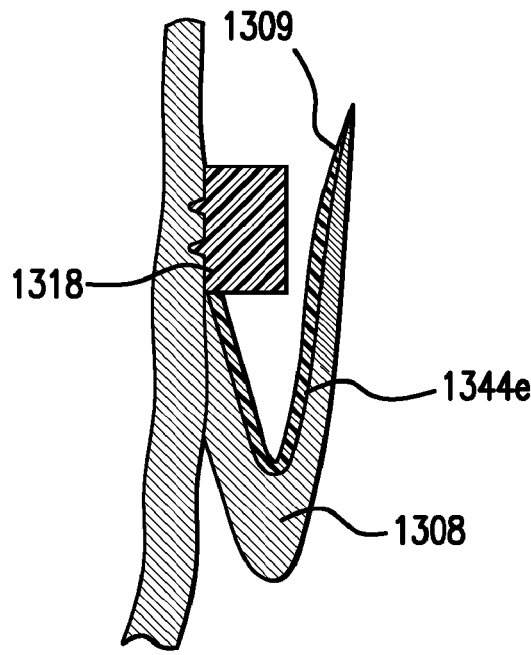
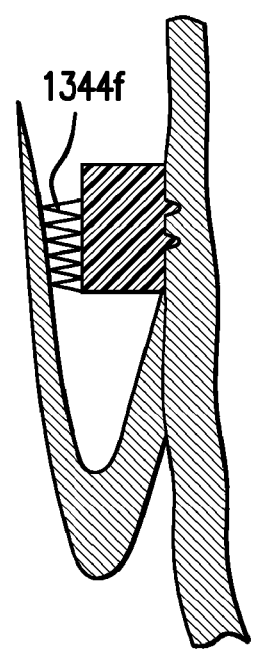
FIG.13e  FIG.13f
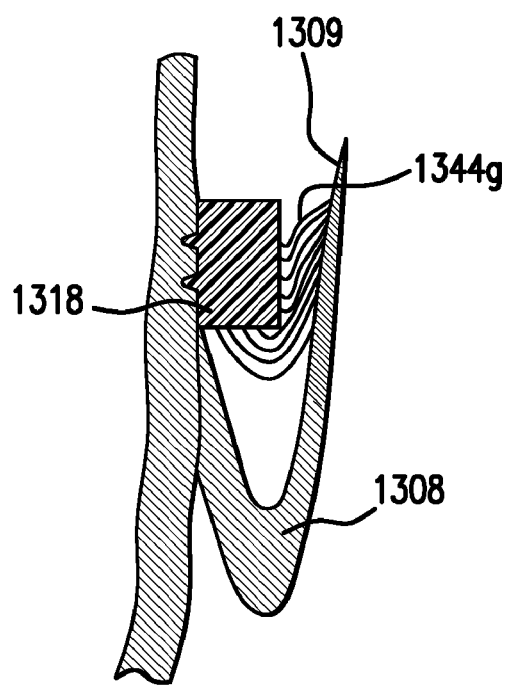
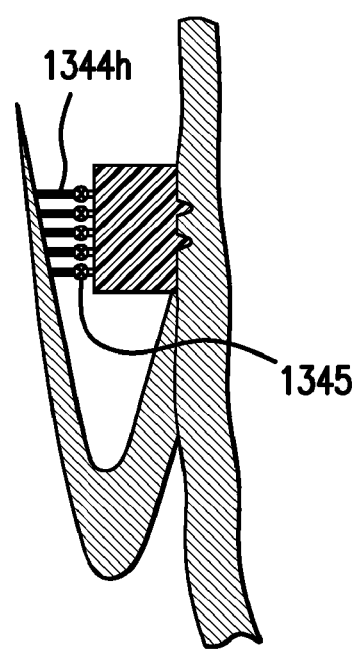
FIG.13g  FIG.13h

PROVIDING AT LEAST ONE MEDICAL DEVICE
INCLUDING A THERAPEUTIC AGENT
(S1)

SECURING THE AT LEAST ONE MEDICAL DEVICE
WITHIN THE LUMEN
(S2)

RELEASING THERAPEUTIC AGENT
(S3)

DELIVERING THE THERAPEUTIC AGENT TO A TARGET
PORTION OF THE HEART VALVE WHEN THE HEART
VALVE OPENS
(S4)

FIG.18

LOCAL DELIVERY OF THERAPEUTIC AGENT TO HEART VALVES

RELATED APPLICATIONS

This application claims benefit of U.S. Provisional Application No. 60/898,099, filed Jan. 30, 2007, which is incorporated herein in its entirety.

TECHNICAL FIELD

The present invention generally relates to the treatment of diseased or damaged heart valves.

BACKGROUND

Diseased and damaged heart valves pose a serious health problem. Hundreds of thousands of surgeries are performed annually to repair heart valves. The functional properties of heart valves include, but are not limited to, preventing backflow from one chamber to another or between a vessel and a chamber, permitting rapid flow of fluid without imposing resistance on that flow, and withstanding high-pressure loads.

The four heart valves include the tricuspid valve at the exit of the right atrium, the pulmonary valve at the exit of the right ventricle, the mitral valve at the exit of the left atrium, and the aortic valve at the exit of the left ventricle. All four heart valves are generally passive structures that typically do not perform any active contractile function. Each heart valve includes movable leaflets that are designed to open and close in response to differential pressures on either side of the valve. Fluid flows from areas of high pressure to areas of low pressure, and, in the heart, the valves open and close in response to pressure changes. For example, the valves open when pressure in the preceding chamber is higher and close when the pressure in the preceding chamber is lower.

Thus, the valves in the heart help maintain the physiologic direction of fluid flow (e.g., blood flow) via the right atrium-right ventricle-lungs-left atrium-left ventricle-aorta. Although each of these valves has a slightly different structure, they serve similar functions. As stated above, one of those functions is to prevent backflow of fluid. Backflow prevention facilitates the proper direction of flow through the circulatory system and reduces the amount of work the heart must do to pump blood through the system.

There are numerous complications and diseases of the heart valves that can occur. Heart valves may become dysfunctional from inflammation, autoimmune disease, and or calcification. For example, stenosis or hardening of the valve can prevent the valve from fully opening or closing. Therefore, as a result of stenosis, backflow can occur. Consequently, surgery may be necessary to repair or treat damaged or diseased heart valves.

BRIEF DESCRIPTION

The present invention is directed to an implantable medical device and methods for delivering therapeutic agent from the medical device to treat heart valves. In accordance with the embodiments of the present invention, for example, some or all of the surfaces of a heart valve, such as the aortic valve, may be treated with therapeutic agent via local delivery from the implantable medical device.

In accordance with one embodiment of the present invention, an implantable medical device is provided. In this embodiment, the medical device may be implantable proximate to a heart valve. The medical device may comprise a body having first and second sections. The first section or at least a portion thereof may include therapeutic agent which releases over time. The second section can be configured to support the device and may be located downstream from the heart valve and the first section.

In another embodiment, a method for delivery of therapeutic agent to a heart valve is provided. The method may include providing at least one medical device having a body with first and second sections wherein at least the first section includes therapeutic agent which releases over time. The method may include positioning the medical device in a location proximate to a downstream surface of the heart valve and implanting the device. The therapeutic agent released may then be concentrated and delivered to a target portion of the heart valve when the heart valve opens.

The invention may be embodied in numerous devices and through numerous methods and systems. The following detailed description, taken in conjunction with the annexed drawings, discloses examples of the invention. Other embodiments, which incorporate some or all of the features as taught herein, are also possible.

BRIEF DESCRIPTION OF THE DRAWINGS

Referring to the drawings, which form a part of this disclosure:

FIGS. 13a-h show cross-sectional views of various medical devices contacting an open heart valve as may be employed in accordance with embodiments of the present invention;

FIG. 18 shows a method for treating a heart valve in accordance with an embodiment of the present invention.

DETAILED DESCRIPTION

Figure 1:
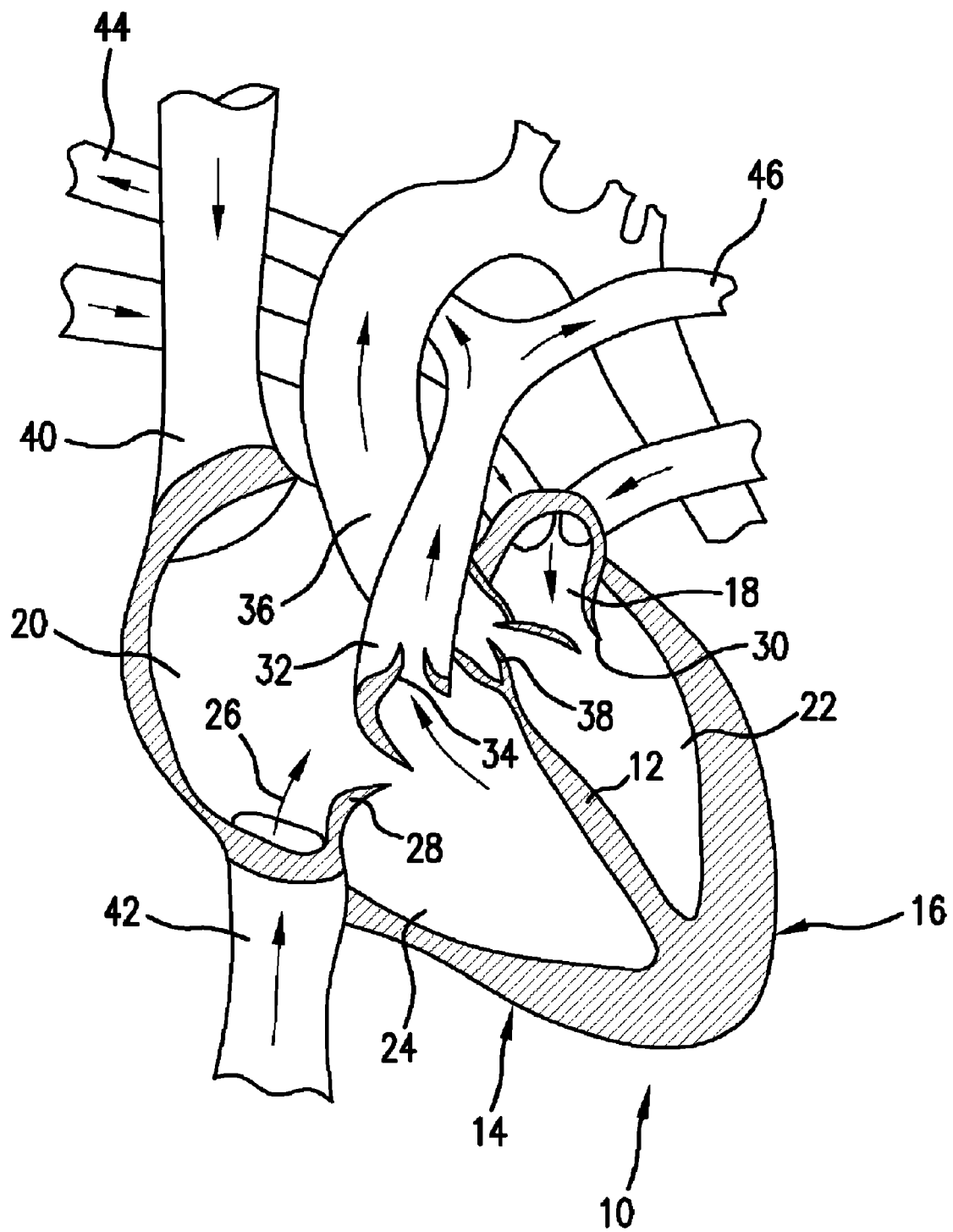
FIG. 1 shows a cross-sectional view of a human heart.

The present invention is directed to a implantable medical device and methods that employ these medical devices to treat damaged or diseased heart valves. The heart valves may be dysfunctional due to conditions such as inflammation, autoimmune disease, and/or calcification. This medical device and methods that employ the device may be used to deliver therapeutic agent to the heart valve (for example to the valve leaflets), indirectly, directly, or in a manner using both indirect and direct delivery. This valve treatment can improve valve function, and, correspondingly, improve the function of the heart. For example, therapeutic agents such as statins, steroids, de-calcification agents, and ACE inhibitors may be delivered to improve or slow valve dysfunction.

The medical device may be of various contours, sizes, and shapes. The characteristics of the medical device may be determined based upon the anatomy of an individual patient and the severity of the valve damage or disease.

The medical device may be filled or coated with therapeutic agent and/or polymers configured to contain, control, or modulate release of the therapeutic agent. Therefore, the therapeutic agent elutes from the medical device for a controlled localized release. The coating can be a polymer-therapeutic agent combination or mixture (e.g., layers of polymer and therapeutic agent), or only therapeutic agent.

The medical device may carry therapeutic agent in a porous matrix which comprises a portion or a layer of the device. The medical device may also be entirely porous. The matrix may be loaded with therapeutic agent by any suitable injection device such as a syringe. In other instances, the medical device may be coated with therapeutic agent using conventional techniques such as spraying or dipping. Other combinations of porous regions loaded with therapeutic agent and therapeutic agent coatings are possible.

The medical device may have a generally tubular body with first and second sections. The first section may comprise the delivery section and the second section may comprise the support section. The first section may comprise therapeutic agent which elutes over time and may be designed to maximize drug loading, release, and delivery. The support section may be positioned and/or designed to secure the implant so that any interference with the coronary arteries or heart valve may be minimized. The support section may be loaded or coated with the same or different therapeutic agent as that of the delivery section. For example, the support section may be loaded with a therapeutic agent which minimizes the occurrence of stenosis, restenosis, or hyper-proliferation in response to the implant. The support section may also be free of therapeutic agent. In some instances, the delivery section alone may be sufficient to secure the implant, in which case the implant may be provided with only a delivery section and no support section.

The methods employed in accordance with embodiments of the present invention use medical devices which are infused, injected, coated or otherwise loaded with therapeutic agent and positioned proximate to a heart valve. In certain embodiments, as the heart valve allows fluid flow, the implanted medical device utilizes a re-circulating fluid (blood) pool to facilitate the indirect transfer of therapeutic agent from the medical device to a target portion of the heart valve. This re-circulation of fluid maintains higher concentrations of therapeutic agent proximate to a target portion of the heart valve. For example, the medical device may be positioned so that the concentration of therapeutic agent may be higher proximate to the downstream side of the valve leaflet. In certain embodiments, the open valve may directly contact the medical device allowing direct transfer of therapeutic agent from the medical device to the valve.

Because a basic understanding of the anatomy of the heart is helpful for understanding the present invention, the basic physiology will be described in detail with reference to FIGS. 1 and 2. The heart 10 is a hollow, cone-shaped muscle located between the lungs and behind the sternum. Approximately two-thirds of the heart is located to the left of the midline of the body and one-third to the right. The heart is divided into the following four chambers: right atrium 20, right ventricle 24, left atrium 18, and left ventricle 22. Each chamber has a one-way valve at its exit that prevents blood from flowing backwards. When each chamber contracts the valve at its exit opens. When it is finished contracting the valve closes so that blood does not flow backwards.

Figure 2:
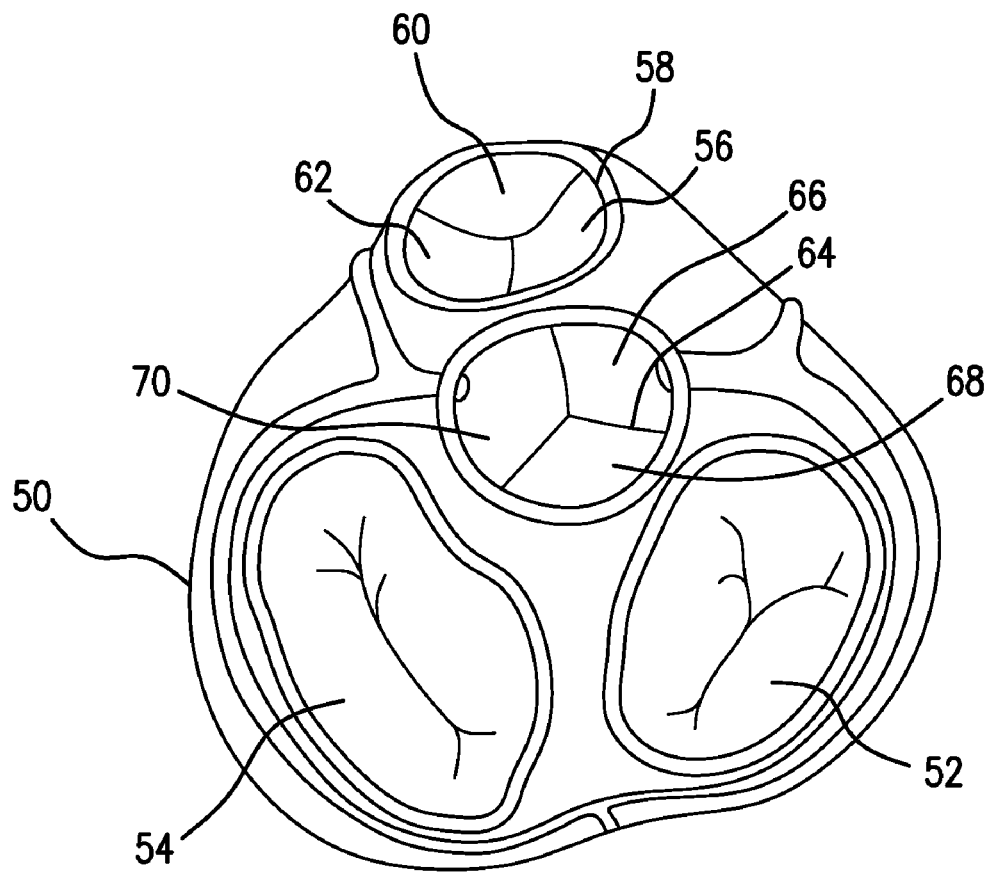
FIG. 2 shows another view of a human heart including the four heart valves.

FIG. 1 illustrates a partially sectioned view of a human heart 10, and its associated vasculature. The heart 10 is subdivided by muscular septum 12 into two lateral halves, which are named respectively right 14 and left 16. A transverse constriction subdivides each half of the heart into two cavities, or chambers. The upper chambers consist of the left and right atria 18, 20 which collect blood. The lower chambers consist of the left and right ventricles 22, 24 which pump blood. The arrows 26 indicate the direction of blood flow through the heart. The right atrium 20 communicates with the right ventricle 24 by the tricuspid valve 28. The left atrium 18 communicates with the left ventricle 22 by the mitral valve 30. The right ventricle 24 empties into the pulmonary artery 32 by way of the pulmonary valve 34. The left ventricle 22 empties into the aorta 36 by way of the aortic valve 38.

The circulation of the heart 10 comprises two components. First is the functional circulation of the heart 10, i.e., the blood flow through the heart 10 from which blood is pumped to the lungs and the body in general. Second is the coronary circulation, i.e., the actual blood supply to the structures and muscles of the heart 10 itself. The functional circulation of the heart 10 pumps blood to the body in general, i.e., the systematic circulation, and to the lungs for oxygenation, i.e., the pulmonic and pulmonary circulation.

The left side 16 of the heart 10 supplies the systematic circulation. The right side 14 of the heart supplies the lungs with blood for oxygenation. Deoxygenated blood from the systematic circulation is returned to the heart 10 and is supplied to the right atrium 20 by the superior and inferior venae cavae 40, 42. The heart 10 pumps the deoxygenated blood into the lungs for oxygenation by way of the main pulmonary artery 32. The main pulmonary artery 32 separates into the right and left pulmonary arteries, 44, 46 which circulate to the right and left lungs, respectively. Oxygenated blood returns to the heart 10 at the left atrium 18 via four pulmonary veins 48 (of which two are shown). The blood then flows to the left ventricle 22 where it is pumped into the aorta 36, which supplies the body with oxygenated blood.

The geometry of the aorta cusp, which is a transition area of the vessel between the aorta and the left ventricle, slightly bulges just distal or downstream of the aortic valve. This bulge has a slightly enlarged vessel inner diameter as compared to the vessel inner diameter of the aorta. Thus, in certain embodiments of the invention, the geometry of the medical device may be matched to the vessel geometry to assist in securing the medical device to prevent migration from the aortic cusp into the aorta.

Turning to the two cardiac valves that function to permit blood flow out of the heart to the lungs (the pulmonary valve) or to the aorta (aortic valve), reference will now be made to FIG. 2. FIG. 2 shows a cross-sectional cutaway depiction of a normal heart 50, illustrating the four valves of the heart, namely the mitral valve assembly 54, tricuspid valve assembly 52, pulmonary valve 58, and aortic valve 64. The aortic valve 64 and pulmonary valve 58 are referred to as semi-lunar valves because of the unique appearance of their leaflets, which are also termed cusps and are shaped like a half-moon. Each of the semi-lunar valves includes three valve leaflets.

The aortic valve 64 includes valve leaflets 66, 68, 70 that respond to pressure differentials between the left ventricle and the aorta. When the left ventricle contracts, the aortic valve leaflets 66, 68, and 70 open to allow the flow of oxygenated blood from the left ventricle into the aorta. When the left ventricle relaxes, the aortic valve leaflets 66, 68, 70 re-approximate to prevent the blood that has entered the aorta from leaking (regurgitating) back into the left ventricle. The pulmonary valve 58 includes leaflets 56, 60, 62 that respond passively in the same manner in response to relaxation and contraction of the right ventricle in moving de-oxygenated blood into the pulmonary artery and thence to the lungs for re-oxygenation.

The valves in the heart thus maintain the physiologic direction of blood flow, namely: right atrium-right ventricle-lungs-left atrium-left ventricle-aorta.

Figure 3:
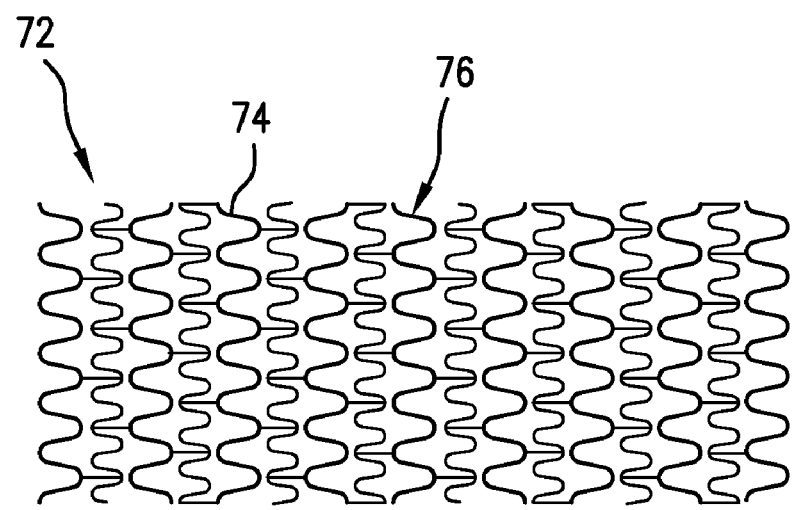
FIG. 3 shows a side-view of a stent, which is a medical device that may be employed in accordance with an embodiment of the present invention.

In accordance with the invention, the medical device provided for implantation and delivery of therapeutic agent to treat the target portion of the heart valve or valves may have any suitable geometry and may be any suitable medical device. For example, as seen in FIG. 3, a stent 72 is illustrated. The stent 72 has a generally tubular lattice portion 76 with an inner diameter and an outer diameter. The individual struts 74 of the lattice portion may include inner surfaces, outer surfaces, and cut faces.

Examples of medical implants that may be suitable for embodiments of the invention include stents, cuffs, coated stents, stent grafts, vascular grafts, intraluminal paving systems, and other devices used in connection with therapeutic agents.

The medical implants themselves may be self-expanding, mechanically expandable, or hybrid implants which may have both self-expanding and mechanically expandable characteristics. Mechanical or expandable medical devices may aid in traversing the narrower peripheral arteries and allow for expansion to the appropriate size/geometry when the targeted vessel lumen, such as the aorta, is reached.

The medical implant may be made from a variety of materials, including plastics and metals. For example, the implant may be a low radial force self-expanding biodegradable polymer or magnesium drug eluting stent, cuff, or coil.

Figure 4A:
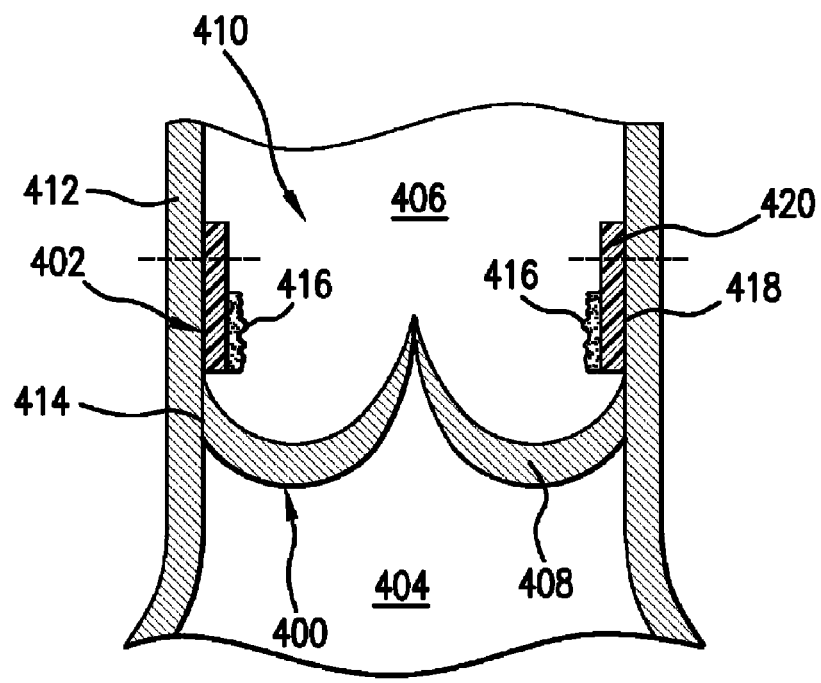
FIG. 4a shows a cross-sectional view of medical device implanted within a vessel lumen, with a heart valve being illustrated in a closed position in accordance with an embodiment of the present invention.

Referring to FIG. 4*a*, a cross-sectional view of a heart valve 400 and a medical implant 402 are shown. In FIG. 4*a* the heart valve 400 is in the closed position. Heart valve 400 is comprised of three valve leaflets 408 (only two are shown). In the embodiment, an upstream 404 and downstream 406 side of the heart valve are labeled. The heart valve leaflets 408 are hingedly connected to wall 412 of the vessel lumen 410 via a root 414. The area between the vessel lumen wall 412 and the downstream side 406 of the valve leaflet 408 may be referred to as the valve leaflet pocket or heart valve pocket.

It can be seen that the medical device 402 is implanted into the vessel lumen 410 on the downstream side 406 of the valve 400. In the example, the medical device 402 is expanded to contact the vessel lumen wall 412 to support the medical device 402. The medical device 402 includes first and second sections 418, 420 and the first section 418 may be coated or injected with therapeutic agent 416.

Figure 4B:
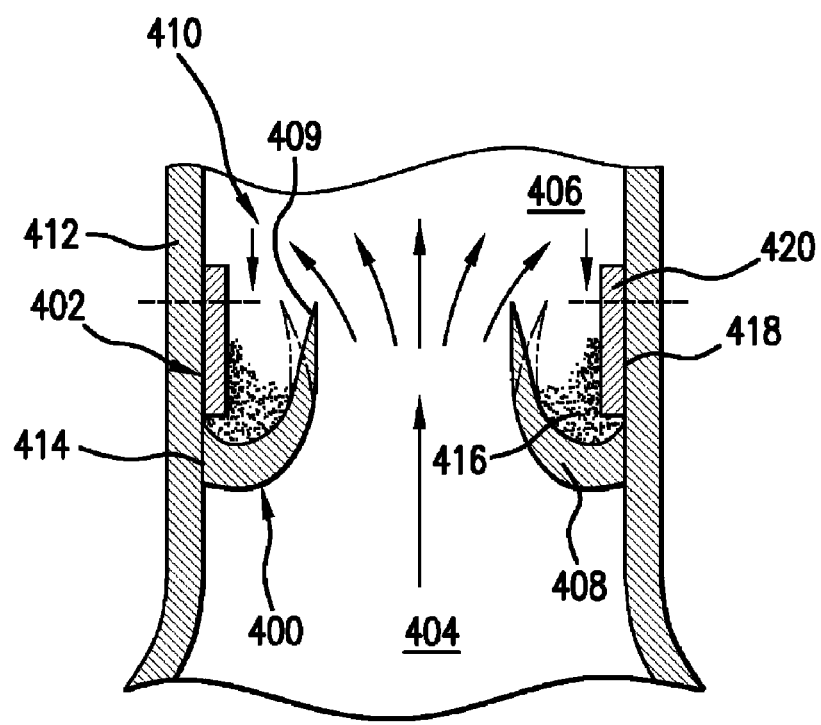
FIG. 4b shows a cross-sectional view similar to FIG. 4a with the heart valve in an open position.

FIG. 4*b* shows the heart valve 400 of FIG. 4*a* in the open position. As can be seen in FIG. 4*b*, fluid flows from the upstream side 404 of the valve 400 to the downstream side 406 of the valve and into the vessel lumen 410. For example, fluid may flow from the left ventricle to the aortic lumen via the aortic valve. Proximate to the downstream surface 409 of the heart valve leaflet 408 and the vessel wall 412, a recirculation of fluid (or backflow) may be created due to turbulent flow. The re-circulating fluid pool may be utilized via positioning the medical device to concentrate therapeutic agent. Also, as shown in phantom, the valve leaflet 408 may also flutter when in the open position.

Figure 5:
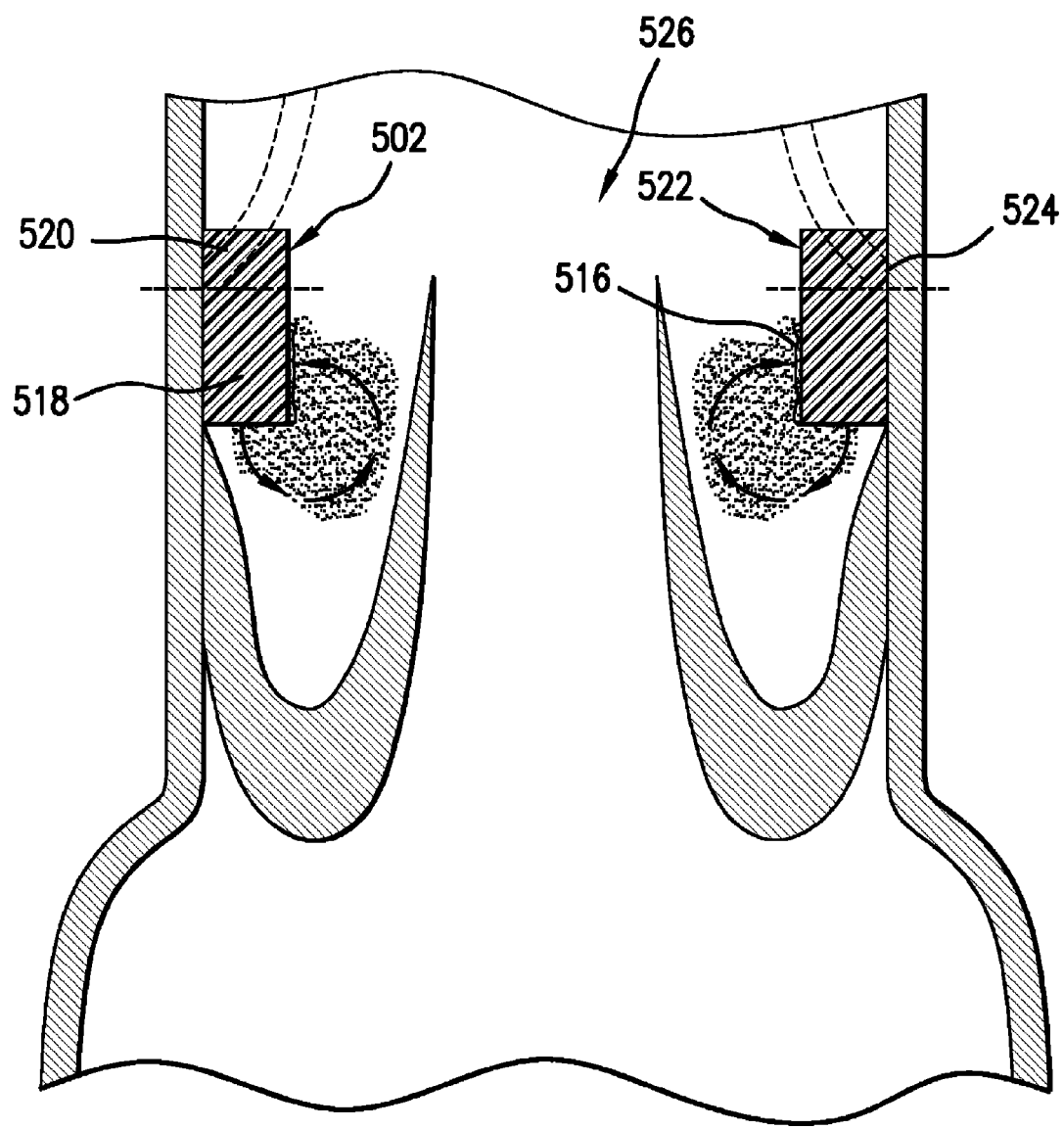
FIG. 5 is a cross-sectional view showing therapeutic agent being transferred from a medical device to a heart valve via fluid recirculation in accordance with an embodiment of the present invention.

Referring now to FIG. 5, a polymeric medical device 502 is shown having a generally tubular body, including an inner diameter 522 and an outer diameter 524 defining a central passageway 526. As stated above, the body may be comprised of first and second sections 518, 520.

The first section 518 may be comprised of any vascularly compatible material which contains therapeutic agent, including, for example, SIBS, PLGA, and SIBS coated on a metal. In the instant case, only the inner diameter of the first section 518 includes therapeutic agent 516; however, the outer diameter and/or cut faces of the medical device may also include therapeutic agent if desired. In addition, portions of the medical device may be made from a porous material such that some or substantial portions of the medical device are infused with a therapeutic agent.

The first and second sections 518, 520 may be unitarily formed or may be separate sections which are integrally attached by adhesives, mechanical attachments, and/or welds. In the latter case, the first section 518 may be removable, refillable, and/or replaceable.

Figure 6:
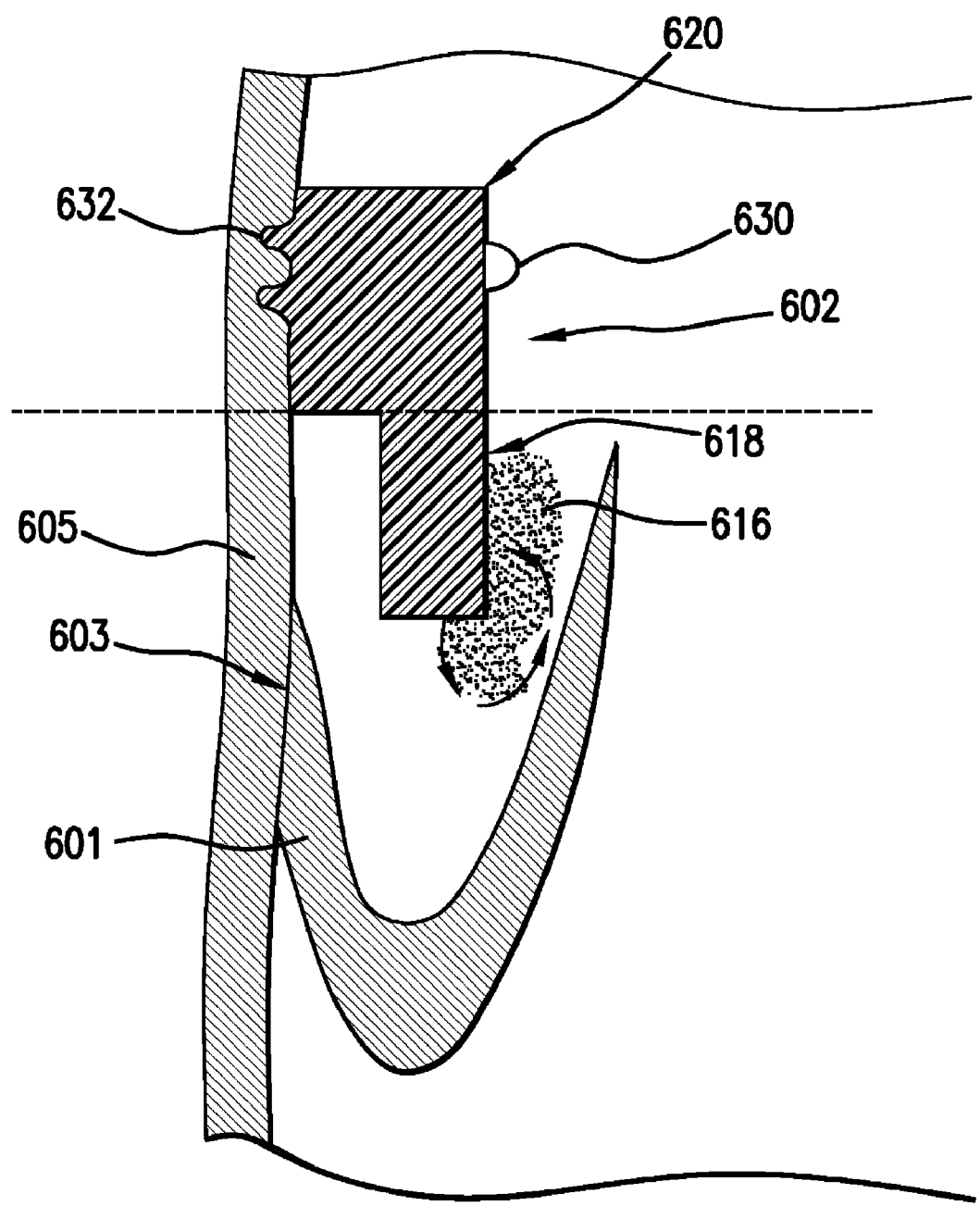
FIG. 6 is a cross-sectional view showing therapeutic agent being transferred from another medical device that may be coated in accordance with an embodiment of the present invention.

FIG. 6 shows another embodiment of the invention in which the first section and second sections 618, 620 are of different configurations. In this example, the first section 618 has a smaller transverse cross-section and therefore a smaller outer diameter than the second section 620. Thus, this configuration, depending on the size of the outer diameter, may allow positioning of the first section 618 closer to the target portion of the heart valve 600 while minimizing interference with the root 603 or hinged connection of the valve leaflet 601.

Also in this embodiment it can be seen that the second section 620 has a removal element on an inner surface. In the instant case the removal element 630 is an eye loop, however, any suitable attachment member, point, or protrusion for a removal tool may be used. In addition, the removal element can be a detent, such as, for example, an indentation in the first or second section, to allow a removal tool to hook or lock into for removal. Other arrangements are plausible. For example, the removal elements 630 may be positioned on the first section 618 to collapse or remove the medical device 602 after the treatment period is complete. This may be desirable if the first section 618 is to be removed, refilled, or replaced.

As can also be seen in FIG. 6, the second section 620 has a support element 632 on an outer diameter. In this example, two barbs are used as support elements 632 to secure the medical device 602 within the vessel lumen wall 605. Although barbs are used in this instance, any suitable support elements 632 may be used including, but not limited to, screws, helical fasteners, barbed shafts, pace maker leads, sutures, and staples. In addition, barbs or other separate support elements 632 may not be necessary to secure the medical device 602 into the vessel wall 605. The expansion pressure may be sufficient to embed the medical device 602 into the vessel wall much the same way that the catheter balloon pressure expands and deforms a stent thereby embedding the stent into a vessel wall without the need for separate support elements. In addition, the geometry of a medical device located downstream of the aortic valve in the aortic cusp may follow the contours of the bulge in the aortic cusp (e.g., phantom lines in FIG. 5), and no or fewer support elements may be used. The support elements 632 may be used to secure the medical device 602 within the valve root 603 or the vessel lumen wall 605.

Any suitable non-toxic bio-stable material or materials may be used for the support and removal elements 630, 632. The material is preferably compatible with the therapeutic agent 616. The material may also be configured to limit tissue in-growth.

Figure 7:
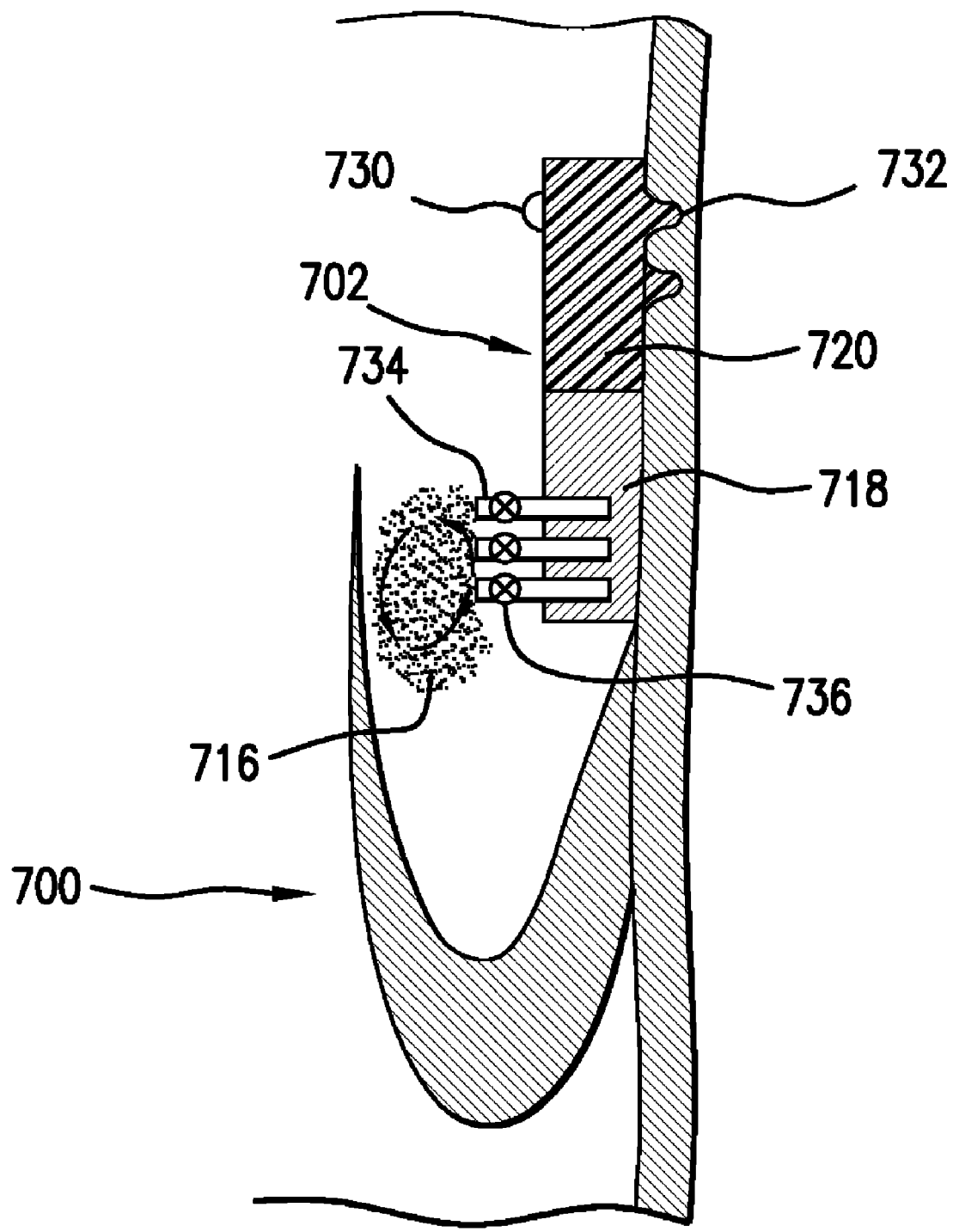
FIG. 7 is a cross-sectional view showing therapeutic agent being transferred from still another medical device that may be used in accordance with an embodiment of the present invention.

FIG. 7 illustrates still another embodiment of a medical device 702 and a heart valve 700 in the open position. In this embodiment, it can be seen that the first section 718 of the medical device 702 may be removable. It is also evident that the first and second sections 718, 720 are made of different materials. More specifically, in the example, the first section 718 may be made of metal and the second section 720 is formed of a polymeric material, however, alternative arrangements are possible. In this case, as described above, the first and second sections 718, 720 may also be provided with removal and support elements 730, 732.

FIG. 7 further shows that the first section 718 may be provided with fibers 734, for example, micro-fibers or nano-fibers. These fibers 734 may be configured to store therapeutic agent 716 until mechanically strained by turbulent flow. For example, a micro-valve 736 may be positioned within each fiber 734 to enable a controlled release of therapeutic agent 716 when the micro-valve 736 is opened due to turbulent flow.

Figure 8A:
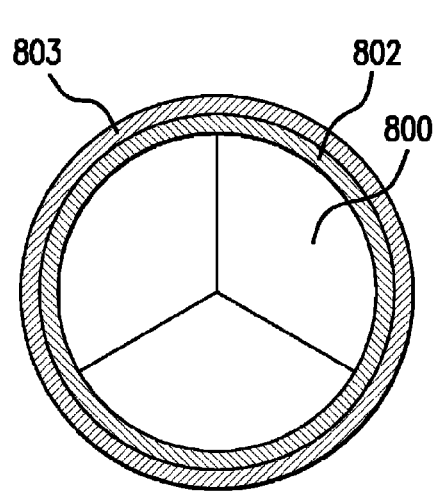
FIG. 8a shows a top-view of a closed heart valve and the medical device of FIG. 4a implanted in accordance with an embodiment of the present invention.
Figure 8B:
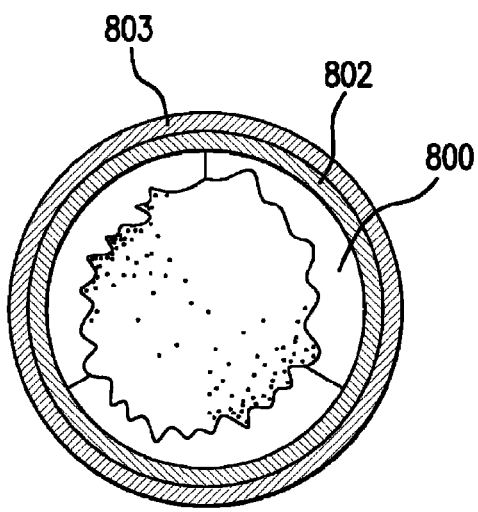
FIG. 8b shows a top-view of a open heart valve and the medical device of FIG. 4a implanted in accordance with an embodiment of the present invention.

FIG. 8*a* shows a top-view or axial view of the implanted medical device 802 of FIG. 4*a* within a closed heart valve 800 in accordance with an embodiment of the present invention. FIG. 8*b* shows a top-view of the medical device 802 of FIG. 4*a* implanted within an open heart valve 800 in accordance with an embodiment of the present invention. As can be seen, the medical device 802 is positioned within the valve leaflet pocket proximate to the valve root 803.

Figure 9:
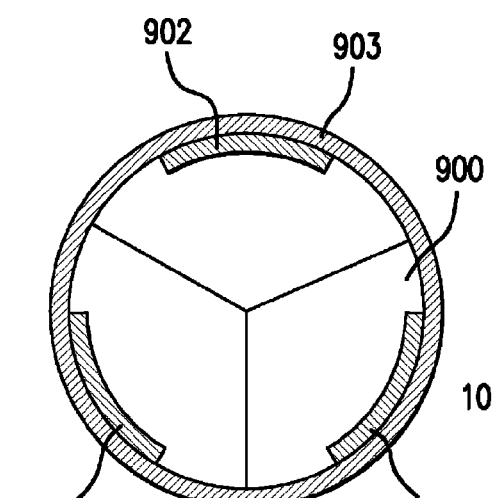
FIG. 9 shows a top-view of a plurality of medical devices implanted adjacent a heart valve in accordance with embodiments of the present invention.

FIG. 9 shows an embodiment wherein a plurality of medical devices 902 are used. In this example, one medical device 902 is used for each valve leaflet pocket. Each medical device 902 extends along a portion of the circumference of the valve opening. Other methodologies may be used as well. Each medical device 902 may be embedded into the vessel wall adjacent the valve leaflet or valve root with support elements, such as barbs, screws, fasteners, sutures, staples and other suitable support elements. The implanted or embedded medical device 902 may release micro-spheres or particles of therapeutic agent.

Figure 10:
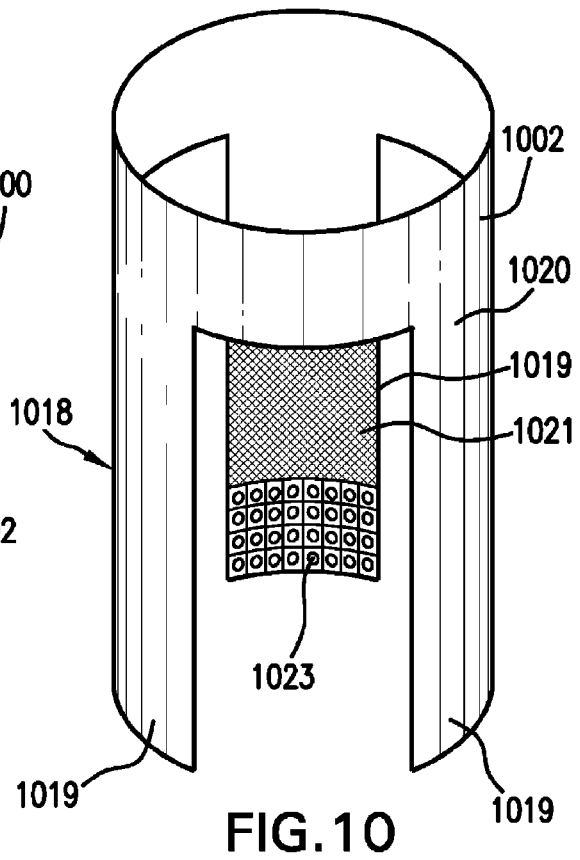
FIG. 10 is a side-view of a medical device having support legs that may be employed in accordance with an embodiment of the present invention.

FIG. 10 shows still another embodiment of the invention (i.e., medical device 1002). In this embodiment, the second section 1020 is a substantially annular band. In FIG. 10 it can be seen that the first section 1018 is comprised of three support legs 1019. Any number of support legs 1019 may be used; however, preferably at least one support leg may be used for each valve leaflet being treated. In use, each support leg 1019 extends upstream into the valve leaflet pockets. The support legs 1019 may be configured such that the space between adjacent legs extends around the connections between adjacent leaflets. Therefore, minimal obstruction of the valve's operation can be achieved. Although support legs 1019 are shown in a generally rectangular shape, the geometry of legs 1019 can take any shape, such as the geometry of the contours of the target valve leaflets. Such geometries may maximize exposure and proximity to targeted leaflets while minimizing interference with leaflet function or the root.

Evident in FIG. 10 is that an inner surface of the support legs 1019 may be roughened 1021 and/or textured 1023 to achieve varying fluid dynamic results. For example, dimples, ridges, or channels may be used to increase turbulent flow, which may result, in certain cases, in increased concentration of therapeutic agent near a target portion of the heart valve.

Figure 11:
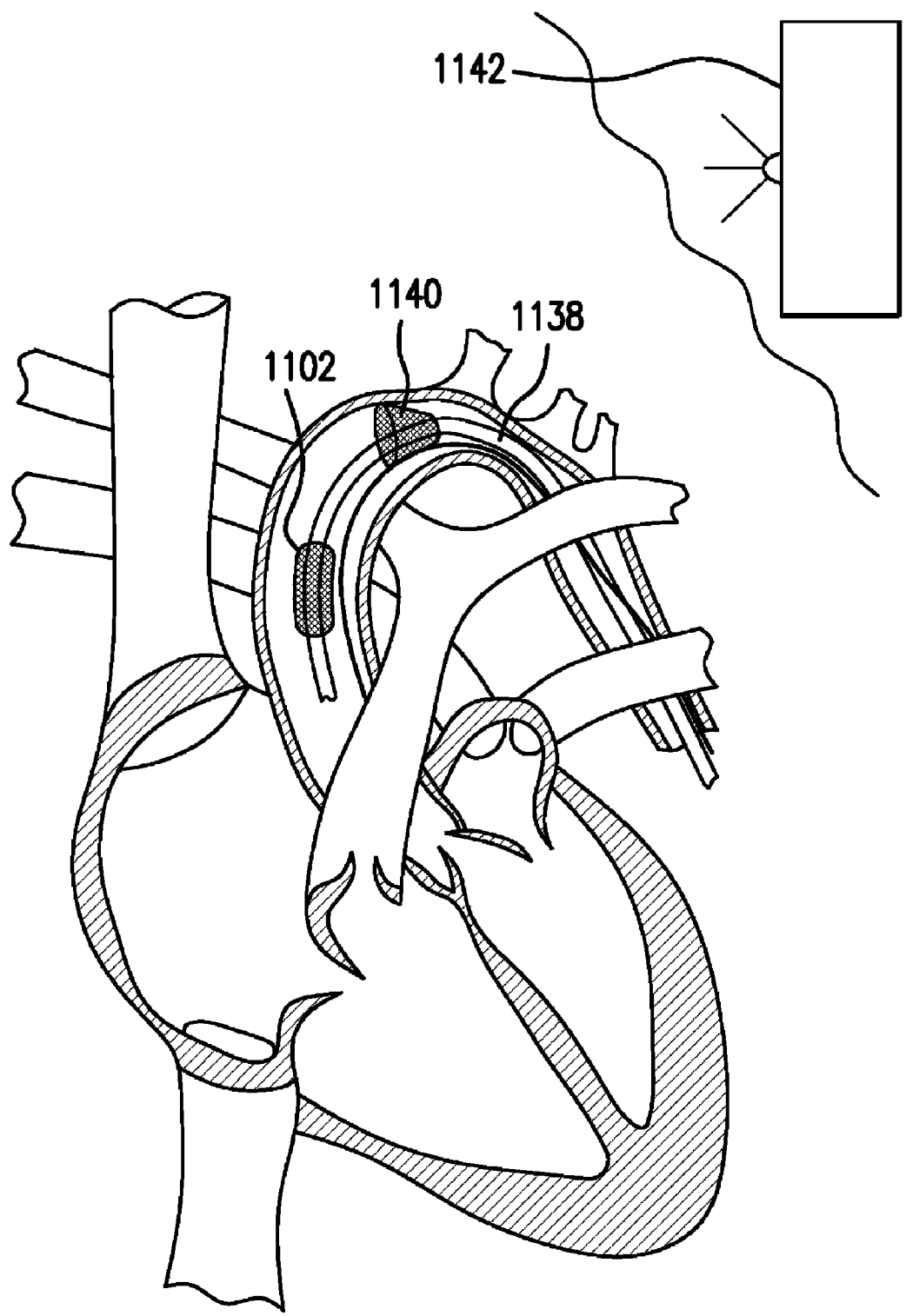
FIG. 11 illustrates a delivery device located within the aorta that may be employed in accordance with an embodiment of the present invention.

Turning to FIG. 11, a positioning device 1138 employed for delivery or removal of the medical device 1102 is shown. The medical device 1102 can be delivered or removed from the vessel lumen through retrograde access, for example, via retrograde access from the arterial tree. Standard techniques may be used for delivering and removing the device. For instance, the medical device 1102 may be positioned on a conventional balloon catheter. The catheter may include an inflatable balloon assembly at the distal end which has a single inflatable balloon member.

In an un-inflated state, the balloon assembly does not significantly increase the overall size of the distal end of the catheter. This allows the distal portion of the catheter to be inserted into the patient and guided through the patient's vasculature to the desired treatment site. Once at the treatment site, the balloon assembly is inflated to position the medical device 1102 against the vessel lumen wall proximate to the treatment site. The balloon assembly can include any number of individual balloons in a number of configurations, depending upon the treatment site. As noted below, suitable imaging devices may be use to orient the positioning device.

As also seen in FIG. 11, the positioning device 1138 may include a filter 1140 which may remove embolic material from the fluid traveling in the lumen to limit the occurrence of ischemic stroke, myocardial infarction, or systemic embolus. Embolic material in this setting is any constituent of blood, or plaque material and superimposed thrombus, which may cause complications in the body if allowed to travel freely in the blood stream. This matter includes, but is not limited to, plaque fragments, fat, platelets, or clots.

Furthermore, FIG. 11 also shows an imaging device 1142 that may facilitate the delivery or removal of the medical device 1102 or portions of the medical device 1102 within the body. For example, to orient the medical device 1102 in relation to the heart valve structure, x-ray fluoroscopy may be required. Therefore, any suitable imaging device 1142 may be used prior to, during, or after the delivery or removal procedure. Suitable imaging devices 1142 include one or more of MRI, echo, CT scanning, and EKG.

Figure 12:
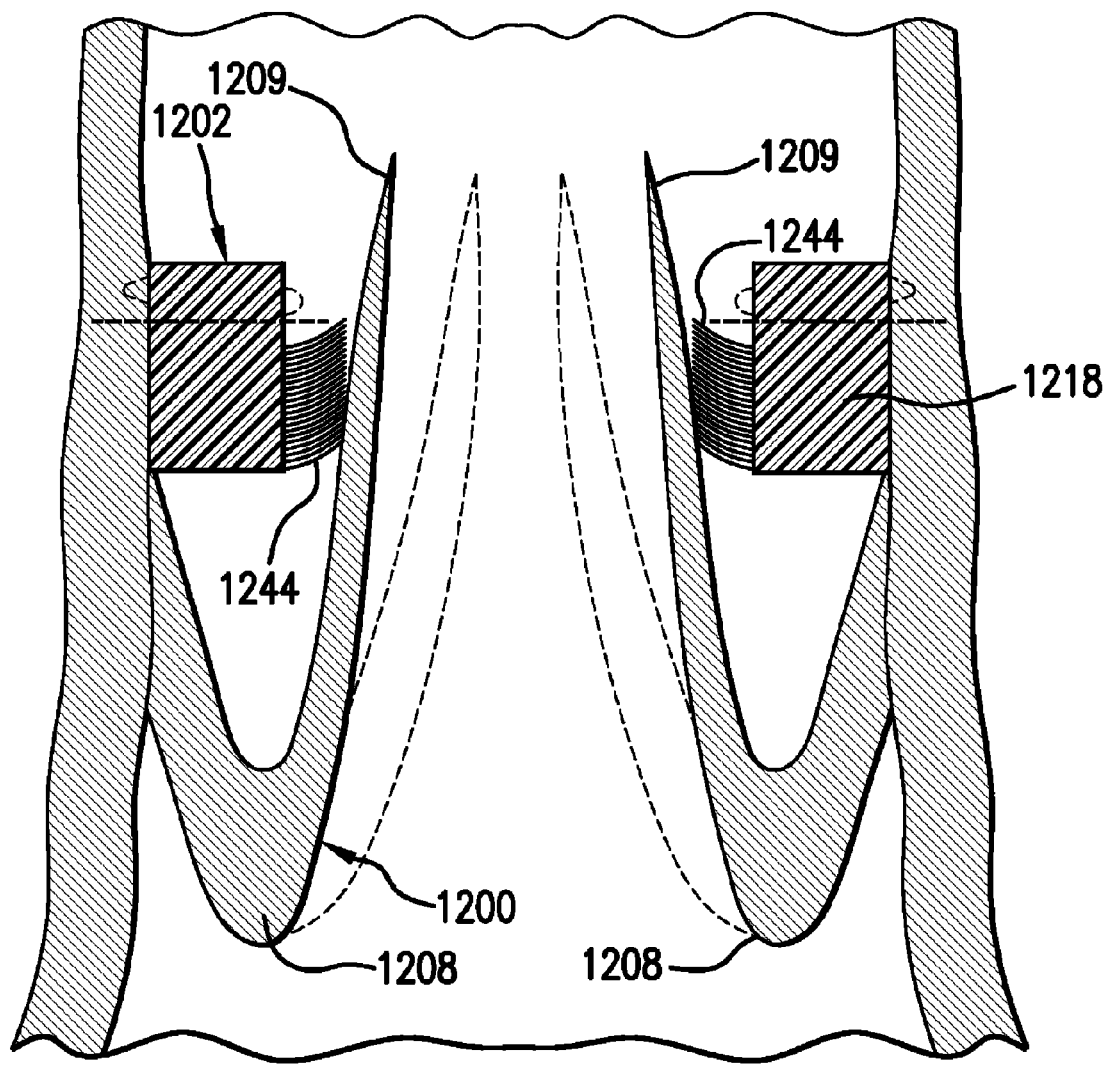
FIG. 12 shows a cross-sectional view of a medical device contacting an open heart valve as may be employed in accordance with an embodiment of the present invention.

FIG. 12 shows another embodiment of the present invention in which the heart valve 1200 is open. The phantom lines show that the heart valve 1200 may also flutter when in the open position. In this embodiment, the medical device 1202 may be positioned so that not only does recirculation of fluid facilitate therapeutic agent transfer, but the positioning of the medical device 1202 may also permit the target portion of the heart valve 1200 to contact the medical device 1202 to deliver therapeutic agent, for example, when the valve 1200 opens and/or flutters.

In this embodiment, the medical device 1202 has one or more contact members 1244. The contact member(s) 1244 may extend inwardly and in the downstream direction so as to not interfere with the function of the heart valve 1200. Furthermore, such an arrangement may facilitate deliver of therapeutic agent towards the vessel lumen and away from the vessel wall. As shown, the contact members 1244 are located on an inner surface of the first section 1218, however, other arrangements are possible. For example, the contact members 1244 may extend from the bottom of the first section or from other surfaces such as the cut faces.

As seen in this embodiment, the inner surface of the first section 1218 is provided with fibers containing or coated with therapeutic agent to contact the downstream surface 1209 of the valve leaflet 1208 when the valve 1200 opens and flutters. The fibers can be highly compliant fibers that contact or brush against the leaflet surface to improve drug delivery. For example, nanofibers, or high compliant polymer fibers may be used. The fibers may be long to encourage contact over most of the cardiac cycle or short to facilitate drug delivery when the valve is in the open position.

FIGS. 13*a-h* illustrate other embodiments that may be used as the contact member for delivering therapeutic agent to a target portion of the heart valve. The various contact members either contain and/or are coated with therapeutic agent.

Figure 13A:
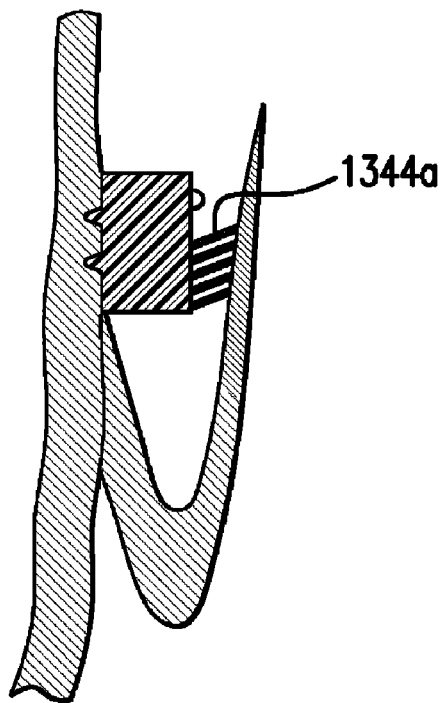

FIG. 13*a* shows a plurality of fins 1344*a* that may extend inwardly and in a downstream direction. Although the fins 1344*a* are illustrated in FIG. 13*a* having a planar direction generally perpendicular to the flow of fluid in the vessel, the fins may also be arranged in a planar direction generally parallel to the flow of fluid in the vessel.

Figure 13B:
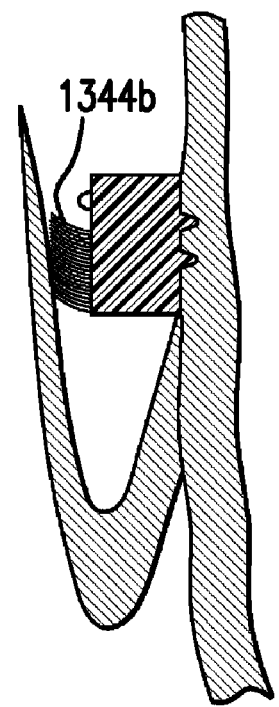

FIG. 13*b* shows a plurality of brushes 1344*b*, which have more rigidity than the aforementioned fibers, which also may extend inwardly and in a downstream direction.

Figure 13C:
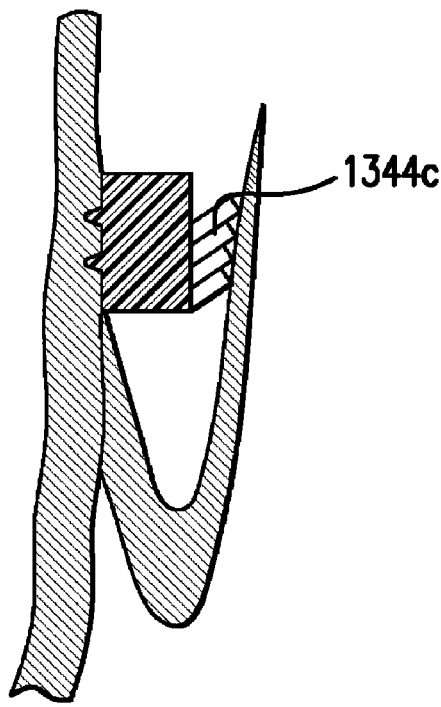
Figure 13D:
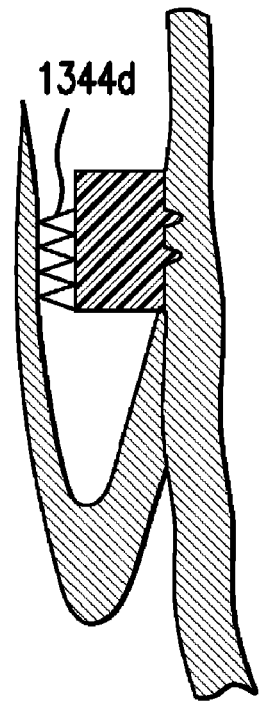

FIG. 13*c* and FIG. 13*d* show ridges 1344*c, d*, respectively. FIG. 13*c* shows substantially round ridges 1344*c*, and FIG. 13*d* shows generally V-shaped ridges 1344*d*. Both ridges 1334*c, d* preferably may extend inwardly and in a downstream direction.

FIG. 13*e* shows a synthetic valve leaflet 1344*e* which may be attached to a side or lower surface of the first section 1318. The synthetic valve leaflet 1344*e* covers all or portions of the downstream surface 1309 of the valve leaflet 1308 to deliver therapeutic agent. The synthetic valve leaflet 1344*e* may also aid in the mechanical function of the valve, such as aiding in the closing of the valve.

FIG. 13*f* shows needles 1344*f* which may be used to contact a target surface of the heart valve. The needles 1344*f* may extend inwardly and downstream and may be coated with or store therapeutic agent for delivery to the downstream surface of the valve leaflet.

FIG. 13*g* shows an embodiment in which fibers 1344*g* may extend from both the inner and proximal surfaces of the first section 1318 to contact a downstream surface 1309 of the valve leaflet 1309.

FIG. 13*h* shows needles 1344*h* which may contain and/or are coated with therapeutic agent for release upon contact with the downstream surface of the heart valve. For example, therapeutic agent may be stored inside the needle. When the needles 1344*h* and heart valve or valve leaflet make contact, a micro-valve 1345 may open to release the therapeutic agent to the valve leaflet.

In alternative arrangements, which are not illustrated, the preceding arrangements and orientations may be modified or combined to improve delivery of therapeutic agent delivery. The arrangements illustrated are merely examples and other configurations are possible.

Figure 14:
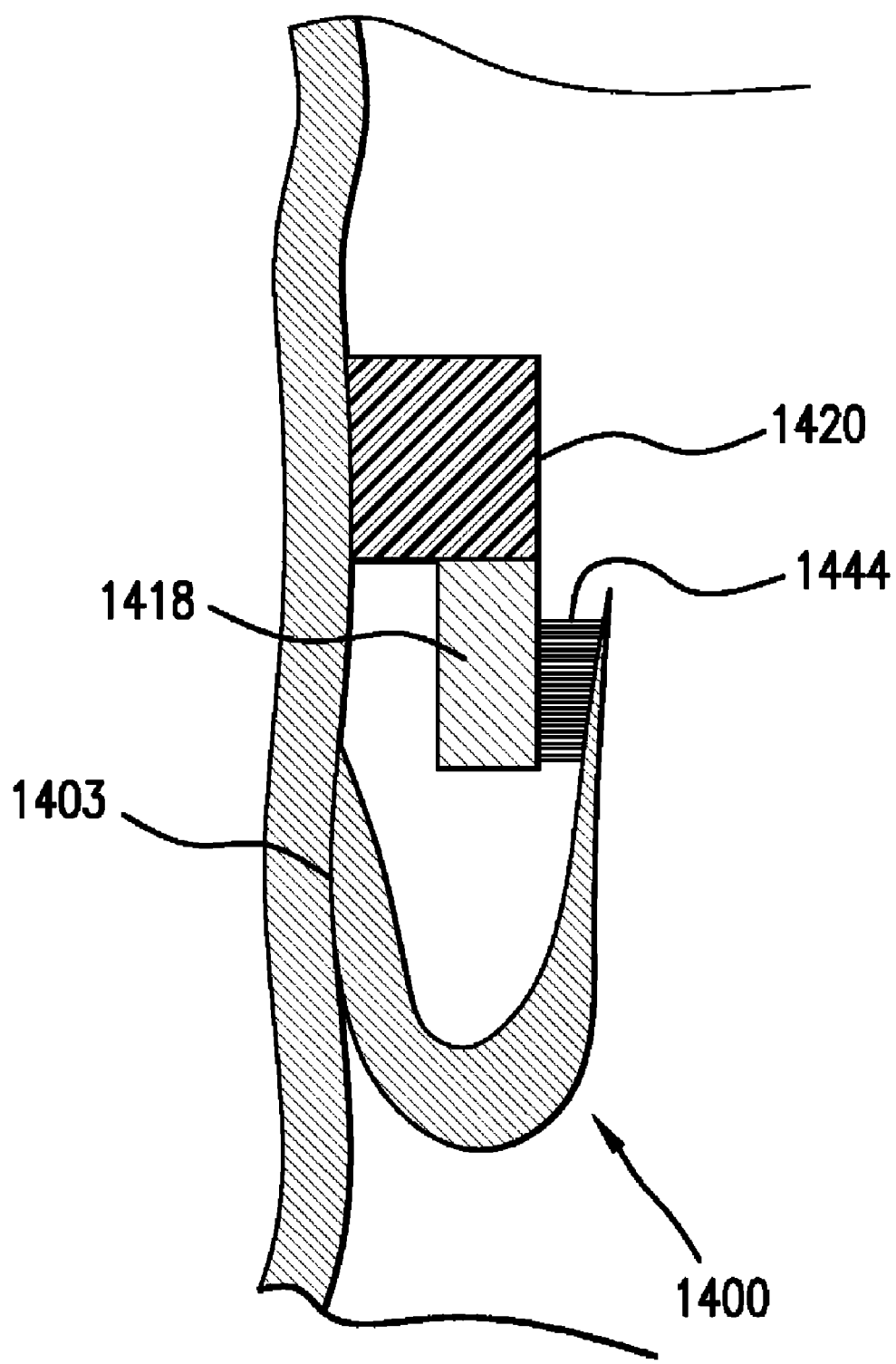
FIG. 14 is a cross-sectional view showing another medical device that may be employed for contacting the heart valve in accordance with an embodiment of the present invention.

FIG. 14 shows a similar embodiment to that of FIG. 12. In this embodiment, the first and second sections 1418, 1420 are of different configurations. In this example, the first section 1418 has a smaller transverse cross-section, and therefore a smaller outer diameter than the second section 1420. This configuration may allow the first section 1418 and the contact members 1444 to be positioned closer to the target portion of the heart valve 1400 without interfering with the root 1403 or hinged connection of the valve leaflet.

Figure 15A:
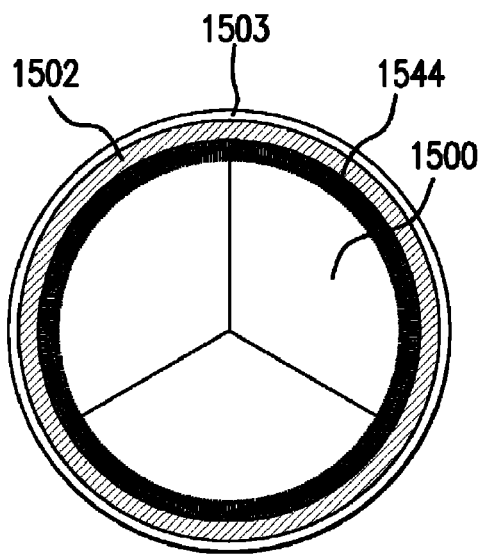
FIG. 15a shows a top-view of the medical device of FIG. 12 implanted within a closed heart valve in accordance with an embodiment of the present invention.
Figure 15B:
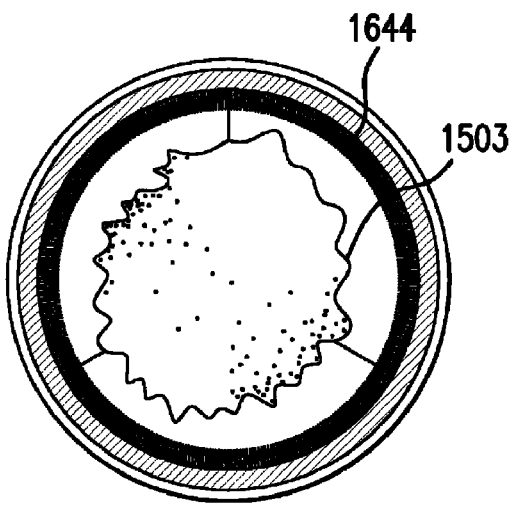
FIG. 15b shows a top-view of the medical device of FIG. 12 implanted within an open heart valve in accordance with an embodiment of the present invention.

FIGS. 15*a-15b* show a top-view or axial view of the medical device 1502 of FIG. 12 implanted within heart valve 1500 in the closed and open positions, respectively. As can be seen, the medical device 1502 is positioned within the valve leaflet pocket proximate to the valve root 1503 and the contact members 1544 extend inwardly towards a longitudinal axis of the valve 1500.

Figure 16:
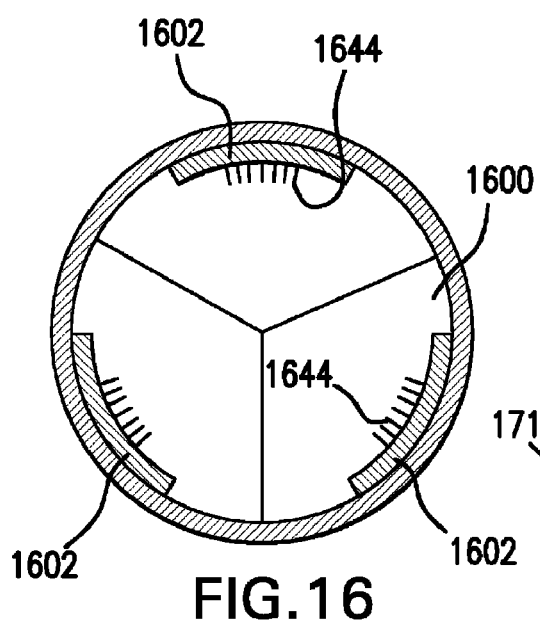
FIG. 16 shows a top-view of a plurality of medical devices implanted within a closed heart valve that may be employed in accordance with embodiments of the present invention.

FIG. 16 shows an embodiment in which a plurality of implants 1602 have inwardly extending contact members 1644 to contact a target portion of the valve 1600. In this example, one medical device 1602 is used for each valve leaflet pocket.

Figure 17:
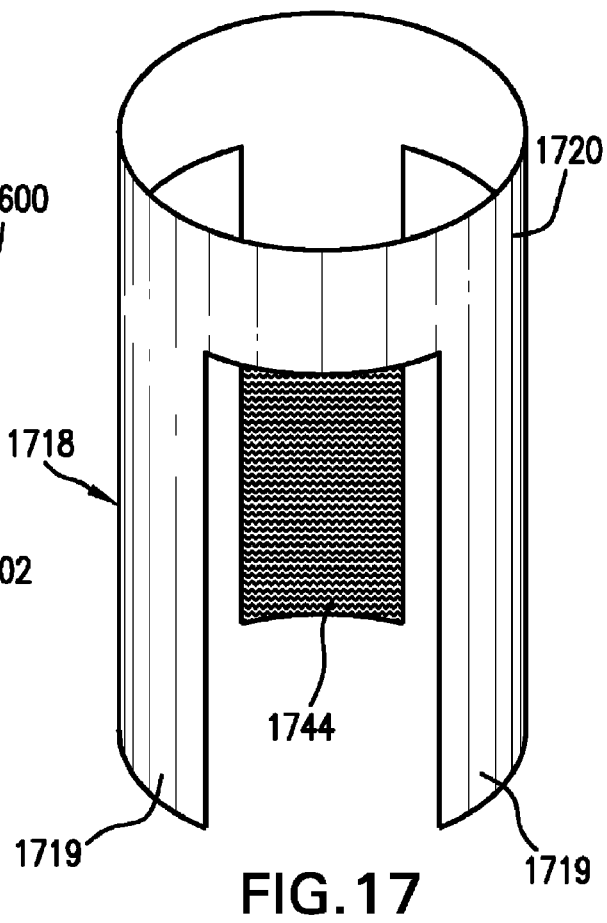
FIG. 17 is a side-view of a medical device having support legs that may be employed in accordance with an embodiment of the present invention.

FIG. 17 shows still another embodiment of the invention. In this embodiment, the second section 1720 may comprise a substantially annular band and the first section 1718 may comprise three support legs 1719. Any number of support legs 1719 may be used; however, in this embodiment, preferably at least one support leg 1719 is used for each valve leaflet being treated. In use, each support leg 1719 extends upstream into the valve leaflet pockets. The first and second sections 1718, 1720 may be configured such that the space between adjacent support legs 1719 extends around the connections between adjacent leaflets to minimize obstruction of the valve operations. Additionally, an inner surface of each support leg 1719 may be provided with one or more contact members 1744 to improve delivery of therapeutic agent to a target portion of the heart valve.

FIG. 18 shows a flow chart including method steps that may be employed with embodiments of the present invention to deliver therapeutic agent from a medical device to a target portion of a heart valve. In the example of FIG. 18, Step S1 may include providing at least one medical device including a therapeutic agent. Step S2 may include securing the at least one medical device within the lumen. Step S3 may include releasing therapeutic agent from the medical device. Step S4 may include delivering the therapeutic agent to a target portion of the heart valve when the heart valve opens. In alternative embodiments, not shown, the sequence of steps may be reordered, and steps may be added or removed. The steps may also be modified. Further, the steps may be repeated in continuous fashion.

In alternative embodiments, not shown, the sequence of steps may be reordered and steps may be added or removed. For example, the medical device may be positioned so as to contact a target portion of the heart valve with a contact member. Further, the steps may be modified and may be repeated in continuous fashion.

While various embodiments have been described, other embodiments are possible. It should be understood that the foregoing descriptions of various examples of the medical device and methods employing these medical devices to deliver therapeutic agent to a heart valve are not intended to be limiting, and any number of modifications, combinations, and alternatives of the examples may be employed to facilitate the effectiveness of localized treatment of heart valves.

The therapeutic agent, in accordance with embodiments of the present invention, may comprise a therapeutic agent formed, for example, by admixing a drug agent with a liquid polymer, in the absence of a solvent, to form a liquid polymer/drug agent mixture. A suitable list of drugs and/or polymer combinations is listed below. The term "therapeutic agent" as used herein includes one or more "therapeutic agents" or "drugs." The terms "therapeutic agents" or "drugs" can be used interchangeably herein and include pharmaceutically active compounds, nucleic acids with and without carrier vectors such as lipids, compacting agents (such as histones), viruses (such as adenovirus, and eno associated virus, retrovirus, lentivirus and α-virus), polymers, hyaluronic acid, proteins, cells and the like, with or without targeting sequences.

Specific examples of therapeutic agents used in conjunction with the present invention include, for example, pharmaceutically active compounds, proteins, cells, oligonucleotides, ribozymes, anti-sense oligonucleotides, DNA compacting agents, gene/vector systems (i.e., any vehicle that allows for the uptake and expression of nucleic acids), nucleic acids (including, for example, recombinant nucleic acids; naked DNA, cDNA, RNA; genomic DNA, cDNA or RNA in a non-infectious vector or in a viral vector and which further may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral, liposomes and cationic and anionic polymers and neutral polymers that are selected from a number of types depending on the desired application. Non-limiting examples of virus vectors or vectors derived from viral sources include adenoviral vectors, herpes simplex vectors, papilloma vectors, adeno-associated vectors, retroviral vectors, and the like. Non-limiting examples of biologically active solutes include anti-thrombogenic agents such as heparin, heparin derivatives, urokinase, and PPACK (dextrophenylalanine proline arginine chloromethylketone); antioxidants such as probucol and retinoic acid; angiogenic and anti-angiogenic agents and factors; anti-proliferative agents such as enoxaprin, angiopeptin, rapamycin, angiopeptin, monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, acetyl salicylic acid, and mesalamine; calcium entry blockers such as verapamil, diltiazem and nifedipine; antineoplastic/anti-proliferative/anti-mitotic agents such as paclitaxel, 5-fluorouracil, methotrexate, doxorubicin, daunorubicin, cyclosporine, cisplatin, vinblastine, vincristine, epothilones, endostatin, angiostatin and thymidine kinase inhibitors; anti-microbials such as triclosan, cephalosporins, aminoglycosides, and nitrofurantoin; anesthetic agents such as lidocaine, bupivacaine, and ropivacaine; nitric oxide (NO) donors such as linsidomine, molsidomine, L-arginine, NO-protein adducts, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Warfarin sodium, Dicumarol, aspirin, prostaglandin inhibitors, platelet inhibitors and tick antiplatelet factors; vascular cell growth promoters such as growth factors, growth factor receptor antagonists, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vasoactive mechanisms; survival genes which protect against cell death, such as anti-apoptotic Bcl-2 family factors and Akt kinase; and combinations thereof. Cells can be of human origin (autologous or allogenic) or from an animal source (xenogeneic), genetically engineered if desired to deliver proteins of interest at the insertion site. Any modifications are routinely made by one skilled in the art.

Polynucleotide sequences useful in practice of the invention include DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules. The polynucleotides can also code for therapeutic proteins or polypeptides. A polypeptide is understood to be any translation product of a polynucleotide regardless of size, and whether glycosylated or not. Therapeutic proteins and polypeptides include as a primary example, those proteins or polypeptides that can compensate for defective or deficient species in an animal, or those that act through toxic effects to limit or remove harmful cells from the body. In addition, the polypeptides or proteins that can be injected, or whose DNA can be incorporated, include without limitation, angiogenic factors and other molecules competent to induce angiogenesis, including acidic and basic fibroblast growth factors, vascular endothelial growth factor, hif-1, epidermal growth factor, transforming growth factor α and β, platelet-derived endothelial growth factor, platelet-derived growth factor, tumor necrosis factor β, hepatocyte growth factor and insulin like growth factor; growth factors; cell cycle inhibitors including CDK inhibitors; anti-restenosis agents, including p15, p16, p18, p19, p21, p27, p53, p57, Rb, nFkB and E2F decoys, thymidine kinase ("TK") and combinations thereof and other agents useful for interfering with cell proliferation, including agents for treating malignancies; and combinations thereof. Still other useful factors, which can be provided as polypeptides or as DNA encoding these polypeptides, include monocyte chemoattractant protein ("MCP-1"), and the family of bone morphogenic proteins ("BMP's"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

As stated above, coatings used with the exemplary embodiments of the present invention may comprise a polymeric material/drug agent matrix formed, for example, by admixing a drug agent with a liquid polymer, in the absence of a solvent, to form a liquid polymer/drug agent mixture. Curing of the mixture typically occurs in-situ. To facilitate curing, a cross-linking or curing agent may be added to the mixture prior to application thereof. Addition of the cross-linking or curing agent to the polymer/drug agent liquid mixture must not occur too far in advance of the application of the mixture in order to avoid over-curing of the mixture prior to application thereof. Curing may also occur in-situ by exposing the polymer/drug agent mixture, after application to the luminal surface, to radiation such as ultraviolet radiation or laser light, heat, or by contact with metabolic fluids such as water at the site where the mixture has been applied to the luminal surface. In coating systems employed in conjunction with the present invention, the polymeric material may be either bioabsorbable or biostable. Any of the polymers described herein that may be formulated as a liquid may be used to form the polymer/drug agent mixture.

The polymer used in the exemplary embodiments of the present invention is preferably capable of absorbing a substantial amount of drug solution. When applied as a coating on a medical device in accordance with the embodiments of the present invention, the dry polymer is typically on the order of from about 1 to about 50 microns thick. In the case of a balloon catheter, the thickness is preferably about 1 to 10 microns thick, and more preferably about 2 to 5 microns. Very thin polymer coatings, e.g., of about 0.2-0.3 microns and much thicker coatings, e.g., more than 10 microns, are also possible. It is also within the scope of the present invention to apply multiple layers of polymer coating onto a medical device. Such multiple layers are of the same or different polymer materials.

The polymer of the present invention may be hydrophilic or hydrophobic, and may be selected from the group consisting of polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof as well as other biodegradable, bioabsorbable and biostable polymers and copolymers.

Coatings from polymer dispersions such as polyurethane dispersions (BAYHYDROL®, etc.) and acrylic latex dispersions are also within the scope of the present invention. The polymer may be a protein polymer, fibrin, collagen and derivatives thereof, polysaccharides such as celluloses, starches, dextrans, alginates and derivatives of these polysaccharides, an extracellular matrix component, hyaluronic acid, or another biologic agent or a suitable mixture of any of these, for example. In one embodiment of the invention, the preferred polymer is polyacrylic acid, available as HYDROPLUS® (Boston Scientific Corporation, Natick, Mass.), and described in U.S. Pat. No. 5,091,205, the disclosure of which is hereby incorporated herein by reference. U.S. Pat. No. 5,091,205 describes medical devices coated with one or more polyisocyanates such that the devices become instantly lubricious when exposed to body fluids. In another preferred embodiment of the invention, the polymer is a copolymer of polylactic acid and polycaprolactone.

The examples described herein are merely illustrative, as numerous other embodiments may be implemented without departing from the spirit and scope of the exemplary embodiments of the present invention. Moreover, while certain features of the invention may be shown on only certain embodiments or configurations, these features may be exchanged, added, and removed from and between the various embodiments or configurations while remaining within the scope of the invention. Likewise, methods described and disclosed may also be performed in various sequences, with some or all of the disclosed steps being performed in a different order than described while still remaining within the spirit and scope of the present invention.

What is claimed is:

1. A method of treating a heart valve, the method comprising:
    providing at least one medical device having a body with at least a portion thereof including a therapeutic agent, the body further comprising:
        a first section including a plurality of support legs, the plurality of support legs being configured such that a space between adjacent legs extends around a connection between adjacent leaflets of the heart valve and a second section;
    positioning the least one medical device so that each support leg fits within a respective valve pocket and the second section extends continuously around an inner vessel wall of a lumen at a location downstream from a heart valve, and the first section extends upstream from the second section towards the heart valve; and
    securing the at least one medical device to the inner vessel wall of the lumen proximate to the heart valve such that the therapeutic agent releases from the body and is delivered to a target portion of the heart valve.

2. The method of claim 1, wherein the therapeutic agent is delivered to the target portion when the heart valve opens.

3. The method of claim 1, wherein the inner surface of each support leg includes dimples, ridges, or channels.

4. The method of claim 1, wherein each support leg is configured to fit within a respective valve pocket of a respective valve leaflet.

5. The method of claim 1, further comprising providing a filter to prevent embolisms.

6. The method of claim 1, wherein the portion of the body including therapeutic is a contact member configured to contact a target portion of the heart valve to deliver therapeutic agent.

7. The method of claim 6, further comprising positioning the contact member to contact the target portion of the heart valve to deliver the therapeutic agent when the heart valve flutters in the open position.

8. The method of claim 6, wherein the contact member extends substantially inward and downstream.

9. The method of claim 6, wherein the contact member includes at least one fiber.

10. The method of claim 6, wherein the contact member includes at least one brush.

11. The method of claim 6, wherein the contact member includes at least one ridge.

12. The method of claim 6, wherein the contact member includes at least one fin.

13. The method of claim 6, wherein the contact member includes at least one needle.

14. The device of claim 1, wherein the target portion is a valve leaflet.

15. The method of claim 1, wherein the first section includes a fiber which retains the therapeutic agent until the fiber is mechanically strained by fluid flow.

16. The device of claim 1, wherein the body includes at least one removal element to facilitate removal of the medical device.

17. The device of claim 1, wherein the body includes at least one support element to facilitate securing of the device.

18. The device of claim 1, wherein the body is expandable to facilitate securing of the device.

19. The device of claim 1, wherein the second section is substantially tubular and the plurality of support legs includes three support legs each configured to extend into a pocket of the heart valve.

* * * * *

UNITED STATES PATENT AND TRADEMARK OFFICE
CERTIFICATE OF CORRECTION

PATENT NO.        : 8,038,709 B2                             Page 1 of 1
APPLICATION NO.   : 12/022413
DATED             : October 18, 2011
INVENTOR(S)       : Maria Palasis It is certified that error appears in the above-identified patent and that said Letters Patent is hereby corrected as shown below:

Column 14, Claim 6, Line 49:  delete "therapeutic" and insert --a therapeutic agent--.

Column 15, Claim 14, Line 1:  delete "device" and insert --method--.

Column 15, Claim 16, Line 6:  delete "device" and insert --method--.

Column 15, Claim 17, Line 9:  delete "device" and insert --method--.

Column 16, Claim 18, Line 1:  delete "device" and insert --method--.

Column 16, Claim 19, Line 3:  delete "device" and insert --method--.

Signed and Sealed this
Twenty-fourth Day of January, 2012

David J. Kappos
*Director of the United States Patent and Trademark Office*